(12) United States Patent
Yamamoto et al.

(10) Patent No.: US 11,096,567 B2
(45) Date of Patent: Aug. 24, 2021

(54) ENDOSCOPE SYSTEM AND METHOD OF MANUFACTURING AN IMAGE CAPTURING MODULE USED IN THE ENDOSCOPE SYSTEM

(71) Applicant: Olympus Corporation, Hachioji (JP)

(72) Inventors: Ken Yamamoto, Tatsuno-machi (JP); Takuro Suyama, Ina (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days.

(21) Appl. No.: 16/662,882

(22) Filed: Oct. 24, 2019

(65) Prior Publication Data
US 2020/0054202 A1 Feb. 20, 2020

Related U.S. Application Data

(63) Continuation of application No. PCT/JP2017/016615, filed on Apr. 26, 2017.

(51) Int. Cl.
*G03B 17/17* (2021.01)
*H04N 5/335* (2011.01)
(Continued)

(52) U.S. Cl.
CPC ............ *A61B 1/051* (2013.01); *A61B 1/0011* (2013.01); *A61B 1/00096* (2013.01);
(Continued)

(58) Field of Classification Search
CPC ........... A61B 1/04; A61B 1/051; A61B 1/128; A61B 1/00; A61B 1/0011; A61B 1/045;
(Continued)

(56) References Cited

U.S. PATENT DOCUMENTS

2012/0220825 A1 8/2012 Kimura
2013/0253272 A1* 9/2013 Takahashi .............. A61B 1/051
600/160

(Continued)

FOREIGN PATENT DOCUMENTS

JP 2007228296 9/2007
JP 4317622 5/2009
(Continued)

OTHER PUBLICATIONS

International Search Report and Written Opinion from corresponding International Application No. PCT/JP2017/016615, dated Aug. 1, 2017.

*Primary Examiner* — Patrick E Demosky
(74) *Attorney, Agent, or Firm* — Scully, Scott, Murphy & Presser, P.C.

(57) ABSTRACT

An endoscope system includes an endoscope having an insertion portion. The endoscope is attached to the proximal end of the insertion portion. An image capturing module is attached to the distal-end portion of an insertion portion. The image capturing module includes a wiring board having a principal surface including first electrodes and second electrodes disposed thereon. An image capturing element includes respective photodetection and reverse surfaces. The reverse surface includes external electrodes and is connected to the first electrodes on the wiring board. A prism having an entrance surface to which light is applied, a reflection surface, and an exit surface in which the exit surface being bonded to the photodetection surface of the image capturing element. A support member is used to support the prism. A layered element including a plurality of elements is layered together and having an upper surface, a lower surface with element electrodes disposed thereon.

9 Claims, 8 Drawing Sheets

(51) Int. Cl.
   *A61B 1/05*        (2006.01)
   *A61B 1/00*        (2006.01)
   *H04N 5/225*       (2006.01)

(52) U.S. Cl.
   CPC ......... *H04N 5/2253* (2013.01); *H04N 5/2254*
                  (2013.01); *H04N 2005/2255* (2013.01)

(58) Field of Classification Search
   CPC .... A61B 1/00009; G02B 23/24; G02B 23/26;
              H04N 5/225; H04N 5/335; H04N 5/378;
              H04N 5/2257; H04N 5/2253; G03B 17/17
   See application file for complete search history.

(56) References Cited

U.S. PATENT DOCUMENTS

2015/0035960 A1\* 2/2015 Nakamura ........... A61B 1/0011
                                                    348/76
2018/0008132 A1\* 1/2018 Sakai ................ A61B 1/00013

FOREIGN PATENT DOCUMENTS

| JP | 2012170765 | 9/2012 |
| JP | 2015042219 | 3/2015 |
| JP | 2015198726 | 11/2015 |
| JP | 2015198726 A | \* 11/2015 |

\* cited by examiner

ENDOSCOPE SYSTEM AND METHOD OF MANUFACTURING AN IMAGE CAPTURING MODULE USED IN THE ENDOSCOPE SYSTEM

CROSS-REFERENCE TO RELATED APPLICATION

This application is a continuation application of PCT Application No. PCT/JP 2017/016615 filed on Apr. 26, 2017, which is hereby incorporated by reference in its entirety.

TECHNICAL FIELD

The disclosed technology relates to an endoscope incorporating an image capturing module disposed on a distal-end portion of an insertion portion. A laterally arrayed image capturing module including an image capturing element and a layered element that are mounted on a wiring board and a method of manufacturing of a laterally arrayed image capturing module are disclosed.

DESCRIPTION OF THE RELATED ART

The development of ultra-small image capturing modules has been underway for making the distal-end portions of endoscopes smaller in diameter and shorter in length. A laterally arrayed image capturing module includes a prism bonded to a photodetection surface of an image capturing element that is mounted on a wiring board.

Japanese Patent 2015-198726 A discloses an endoscope in which a laterally arrayed image capturing device or a laterally arrayed image capturing module is disposed in the distal-end portion of an insertion portion. The image capturing device includes an image capturing element and a multilayer board that are mounted on an image capturing board, with a prism having an exist surface bonded to the image capturing element. The multilayer board includes a plurality of circuit boards whose overhanging portions are disposed in a space, or a dead space, above a reflection surface of the prism. FIG. 10 illustrates the image capturing device in which the circuit boards are held in contact with the reflection surface of the prism.

The circuit boards are held in contact with the prism in order to transmit heat generated by the circuit boards through the prism.

In the laterally arrayed image capturing module, it is important to positionally match the image capturing element and the prism in an optical axis direction for the purpose of setting an optical path length to a predetermined value. For example, if the prism is disposed forwardly of a predetermined position, then the optical path length becomes too short. If the prism is disposed rearwardly of the predetermined position, then the optical path length becomes too long. In any case, the laterally arrayed image capturing module has its optical characteristics impaired.

Image capturing modules are ultra-small to make endoscopes minimally invasive. Therefore, prisms used in ultra-small image capturing modules have exit surfaces that are smaller than a 1 mm square. Since it is necessary to place such an ultra-small prism accurately in a predetermined position, it has not been easy to manufacture image capturing modules and it has not been easy to guarantee the optical characteristics of image capturing modules.

BRIEF SUMMARY OF EMBODIMENTS

The disclosed technology has been made in view of the foregoing.

One aspect of the disclosed technology is directed to an endoscope system comprising an endoscope having an insertion portion. The insertion portion includes opposed respective distal and proximal ends. The endoscope is attached to the proximal end of the insertion portion and an image capturing module is attached to the distal-end portion of an insertion portion. The image capturing module includes a wiring board having a principal surface including first electrodes and second electrodes disposed thereon. An image capturing element having opposed surfaces defined by respective photodetection and reverse surfaces. The reverse surface includes external electrodes that is disposed thereon and is connected to the first electrodes on the wiring board. A prism having an entrance surface to which light is applied, a reflection surface, and an exit surface in which the exit surface being bonded to the photodetection surface of the image capturing element. A support member is used to support the prism. A layered element including a plurality of elements is layered together and having an upper surface, a lower surface with element electrodes disposed thereon, and a plurality of side surfaces. The element electrodes is joined to the second electrodes on the wiring board. At least a portion of the support member is held in abutment against a first side surface among the plurality of side surfaces of the layered element.

Another aspect of the disclosed technology is directed to an endoscope system having an image capturing module. The image capturing module comprises a wiring board having a principal surface including first electrodes and second electrodes disposed thereon. An image capturing element having opposed surfaces defined by respective photodetection and reverse surfaces. The reverse surface includes external electrodes that is connected to the first electrodes on the wiring board. A prism having an entrance surface to which light is applied, a reflection surface, and an exit surface in which the exit surface is bonded to the photodetection surface of the image capturing element. A support member having an adhesion surface parallel to the reflection surface of the prism, an upper holding surface parallel to the principal surface, and an abutment surface perpendicular to the principal surface. The adhesion surface is bonded to the reflection surface of the prism. A layered element including a plurality of elements layered together and having an upper surface, a lower surface with element electrodes disposed thereon, and a plurality of side surfaces. The element electrodes is joined to the second electrodes on the wiring board. At least a portion of the abutment surface of the support member is held in abutment against a first side surface among the plurality of side surfaces of the layered element.

A further aspect of the disclosed technology is directed to an endoscope system having an image capturing module. The image capturing module comprises a wiring board having a principal surface including first electrodes and second electrodes disposed thereon. An image capturing element having opposed surfaces defined by respective photodetection and reverse surfaces. The reverse surface includes external electrodes being connected to the first electrodes on the wiring board. A prism having an entrance surface to which light is applied, a reflection surface, and an exit surface in which the exit surface being bonded to the photodetection surface of the image capturing element. A layered element including a plurality of elements layered together and having an upper surface, a lower surface with element electrodes disposed thereon, and a plurality of side surfaces. The element electrodes being joined to the second electrodes on the wiring board. The prism has a side where the reflection surface and the exit surface thereof intersect with one another. The side is abutting against a first side surface among the plurality of side surfaces of the layered element.

A further aspect of the disclosed technology is directed to an endoscope system having an image capturing module. The image capturing module comprises a wiring board having a principal surface including first electrodes and second electrodes disposed thereon. An image capturing element having opposed surfaces defined by respective photodetection and reverse surfaces. The reverse surface includes external electrodes being connected to the first electrodes on the wiring board. The prism having an entrance surface to which light is applied, a reflection surface, and an exit surface in which the exit surface is bonded to the photodetection surface of the image capturing element. A layered element including a plurality of elements layered together and having an upper surface, a lower surface with element electrodes disposed thereon, and a plurality of side surfaces. The element electrodes being joined to the second electrodes on the wiring board. The prism has an abutment surface parallel to a first side surface among the plurality of side surfaces of the layered element and held in abutment against the first side surface.

Yet, a further aspect of the disclosed technology is directed to a method of manufacturing an endoscope having an image capturing module. The method comprises mounting a layered element including a plurality of elements layered together on a wiring board with electrodes disposed thereon; mounting an image capturing element on the wiring board; applying an uncured adhesive to a photodetection surface of the image capturing element; moving a support member that supports a prism such that at least a portion of the support member abuts against a first side surface of the layered element, and placing the prism on the photodetection surface; and curing the adhesive.

BRIEF DESCRIPTION OF THE DRAWINGS

The technology disclosed herein, in accordance with one or more various embodiments, is described in detail with reference to the following figures. The drawings are provided for purposes of illustration only and merely depict typical or example embodiments of the disclosed technology. These drawings are provided to facilitate the reader's understanding of the disclosed technology and shall not be considered limiting of the breadth, scope, or applicability thereof. It should be noted that for clarity and ease of illustration these drawings are not necessarily made to scale.

DETAILED DESCRIPTION OF THE EMBODIMENTS

Figure 1:
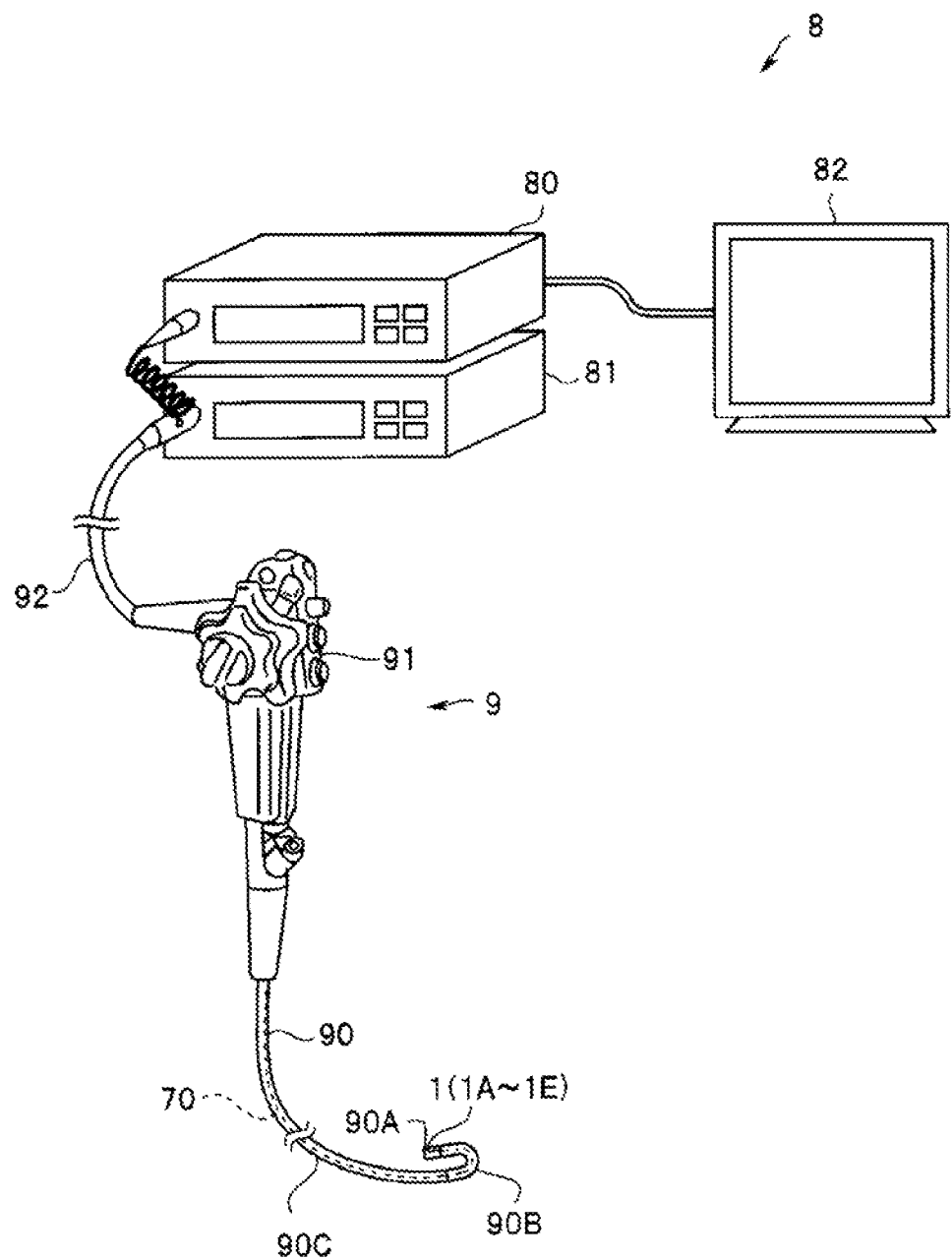
FIG. 1 is a perspective view of an endoscopic system including an endoscope according to a first embodiment.

In the following description, various embodiments of the technology will be described. For purposes of explanation, specific configurations and details are set forth in order to provide a thorough understanding of the embodiments. However, it will also be apparent to one skilled in the art that the technology disclosed herein may be practiced without the specific details. Furthermore, well-known features may be omitted or simplified in order not to obscure the embodiment being described.

It is an object of embodiments of the disclosed technology to provide an endoscope that is minimally invasive, easy to manufacture, and has good optical characteristics, a laterally arrayed image capturing module that is ultra-small and has good optical characteristics, and a method of manufacturing a laterally arrayed image capturing module that is ultra-small and has good optical characteristics.

According to an embodiment of the disclosed technology, there is provided an endoscope having an insertion portion, an operating portion, and a universal cord, and including an image capturing module disposed in a distal-end portion of the insertion portion. The image capturing module includes a wiring board having a principal surface with first electrodes and second electrodes disposed thereon, an image capturing element having a photodetection surface and a reverse surface that is opposite the photodetection surface, with external electrodes on the reverse surface being connected to the first electrodes on the wiring board, a prism having an entrance surface to which light is applied, a reflection surface, and an exit surface, the exit surface being bonded to the photodetection surface of the image capturing element, a support member having an adhesion surface parallel to the reflection surface of the prism, an upper holding surface parallel to the principal surface, and an abutment surface perpendicular to the principal surface, the adhesion surface being bonded to the reflection surface of the prism, and a layered element including a plurality of elements layered together and having an upper surface, a lower surface with element electrodes disposed thereon, and a plurality of side surfaces, the element electrodes being joined to the second electrodes on the wiring board. At least a portion of the abutment surface of the support member is held in abutment against a first side surface among the plurality of side surfaces of the layered element.

According to another embodiment of the disclosed technology, there is provided an image capturing module including a wiring board having a principal surface with first electrodes and second electrodes disposed thereon, an image capturing element having a photodetection surface and a reverse surface that is opposite the photodetection surface, with external electrodes on the reverse surface being connected to the first electrodes on the wiring board, a prism having an entrance surface to which light is applied, a reflection surface, and an exit surface, the exit surface being bonded to the photodetection surface of the image capturing element, a support member having an adhesion surface parallel to the reflection surface of the prism, an upper holding surface parallel to the principal surface, and an abutment surface perpendicular to the principal surface, the adhesion surface being bonded to the reflection surface of the prism, and a layered element including a plurality of elements layered together and having an upper surface, a lower surface with element electrodes disposed thereon, and a plurality of side surfaces, the element electrodes being joined to the second electrodes on the wiring board. At least a portion of the abutment surface of the support member is held in abutment against a first side surface among the plurality of side surfaces of the layered element.

According to still another embodiment of the disclosed technology, there is provided an image capturing module including a wiring board having a principal surface with first electrodes and second electrodes disposed thereon, an image capturing element having a photodetection surface and a reverse surface that is opposite the photodetection surface, with external electrodes on the reverse surface being connected to the first electrodes on the wiring board, a prism having an entrance surface to which light is applied, a reflection surface, and an exit surface, the exit surface being bonded to the photodetection surface of the image capturing element, and a layered element including a plurality of elements layered together and having an upper surface, a lower surface with element electrodes disposed thereon, and a plurality of side surfaces, the element electrodes being joined to the second electrodes on the wiring board. The prism is held in abutment against a first side surface among the plurality of side surfaces of the layered element.

According to yet another embodiment of the disclosed technology, there is provided a method of manufacturing an image capturing module including a wiring board having a principal surface with first electrodes and second electrodes disposed thereon, an image capturing element having a photodetection surface and a reverse surface that is opposite the photodetection surface, with external electrodes on the reverse surface being connected to the first electrodes on the wiring board, a prism having an entrance surface to which light is applied, a reflection surface, and an exit surface, the exit surface being bonded to the photodetection surface of the image capturing element, a support member having an adhesion surface parallel to the reflection surface of the prism, an upper holding surface parallel to the principal surface, and an abutment surface perpendicular to the principal surface, the adhesion surface being bonded to the reflection surface of the prism, and a layered element including a plurality of elements layered together and having an upper surface, a lower surface with element electrodes disposed thereon, and a plurality of side surfaces, the element electrodes being joined to the second electrodes on the wiring board. The method includes a step of mounting the layered element on the wiring board, a step of mounting the image capturing element on the wiring board, a step of applying an uncured adhesive to the photodetection surface of the image capturing element, a step of moving the support member such that at least a portion of the abutment surface abuts against a first side surface of the layered element, and placing the prism on the photodetection surface, and a step of curing the adhesive.

According to the embodiments of the disclosed technology, there are provided an endoscope that is minimally invasive, easy to manufacture, and has good optical characteristics, a laterally arrayed image capturing module that is ultra-small and has good optical characteristics, and a method of manufacturing a laterally arrayed image capturing module that is ultra-small and has good optical characteristics.

First Embodiment

As illustrated in FIG. 1, an endoscopic system 8 including an endoscope 9 according to the present embodiment includes the endoscope 9, a processor 80, a light source device 81, and a monitor 82. The endoscope 9 has an insertion portion 90, an operating portion 91, and a universal cord 92. The endoscope 9 has the insertion portion 90 inserted into a body cavity in an examinee, captures intracorporeal images of the examinee, and outputs image signals.

The insertion portion 90 includes a distal-end portion 90A incorporating an image capturing module 1 disposed therein, a bendable portion 90B joined to a proximal-end side of the distal-end portion 90A and freely bendable, and a soft portion 90C joined to a proximal-end side of the bendable portion 90B. The bendable portion 90B can be bent by an operation of the operating portion 91. The endoscope 9 may be a rigid endoscope.

The operating portion 91 that has various buttons, etc. for operating the endoscope 9 is disposed on a proximal-end side of the insertion portion 90 of the endoscope 9.

The light source device 81 has a white light emitting diode (LED), for example. Illumination light that is emitted by the light source device 81 is guided through a light guide, not illustrated, that extends through the universal cord 92 and the insertion portion 90 to the distal-end portion 90A, illuminating a subject.

The endoscope 9 has the insertion portion 90, the operating portion 91, and the universal cord 92. An image signal that is output from the image capturing module 1 disposed in the distal-end portion 90A of the insertion portion 90 is transmitted through a signal cable 70 extending through the insertion portion 90. Since the image capturing module 1 is ultra-small, the endoscope 9 is minimally invasive with the distal-end portion 90A of the insertion portion 90 being small in diameter.

Furthermore, because the image capturing module 1 is small in size, has good optical characteristics, and is easy to manufacture, as described hereinafter, the endoscope 9 is minimally invasive, has good optical characteristics, and is easy to manufacture.

Second Embodiment

Figure 2:
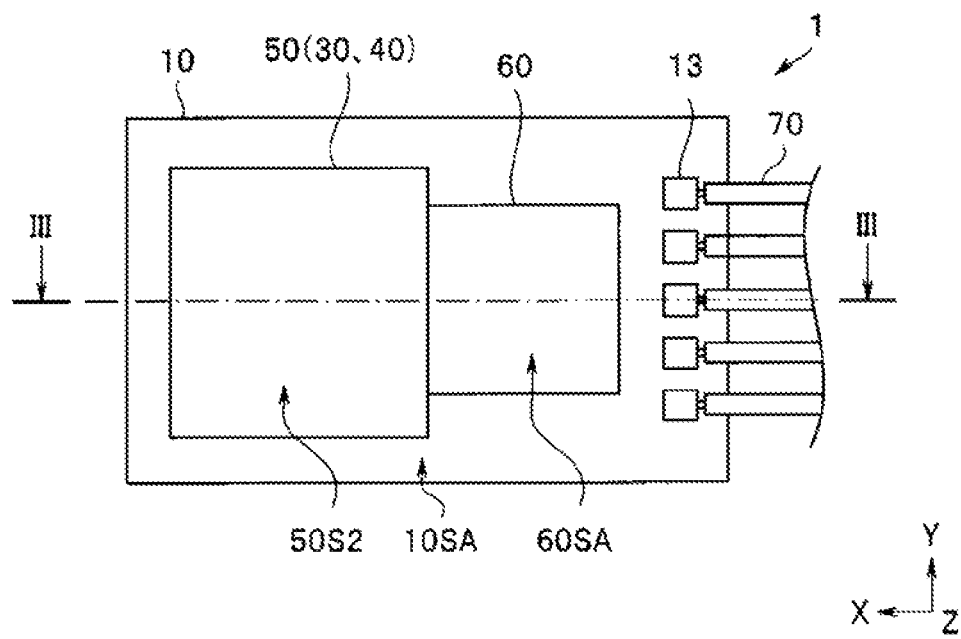
FIG. 2 is a plan view of an image capturing module according to a second embodiment.
Figure 3:
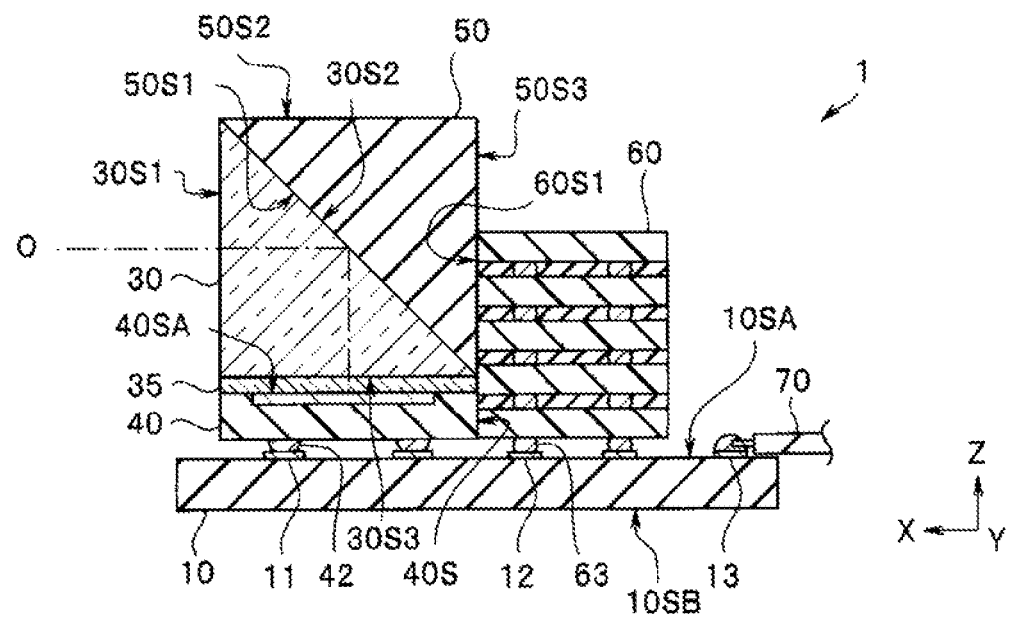
FIG. 3 is a cross-sectional view, taken along line III-III of FIG. 2, of the image capturing module according to the second embodiment.
Figure 4:
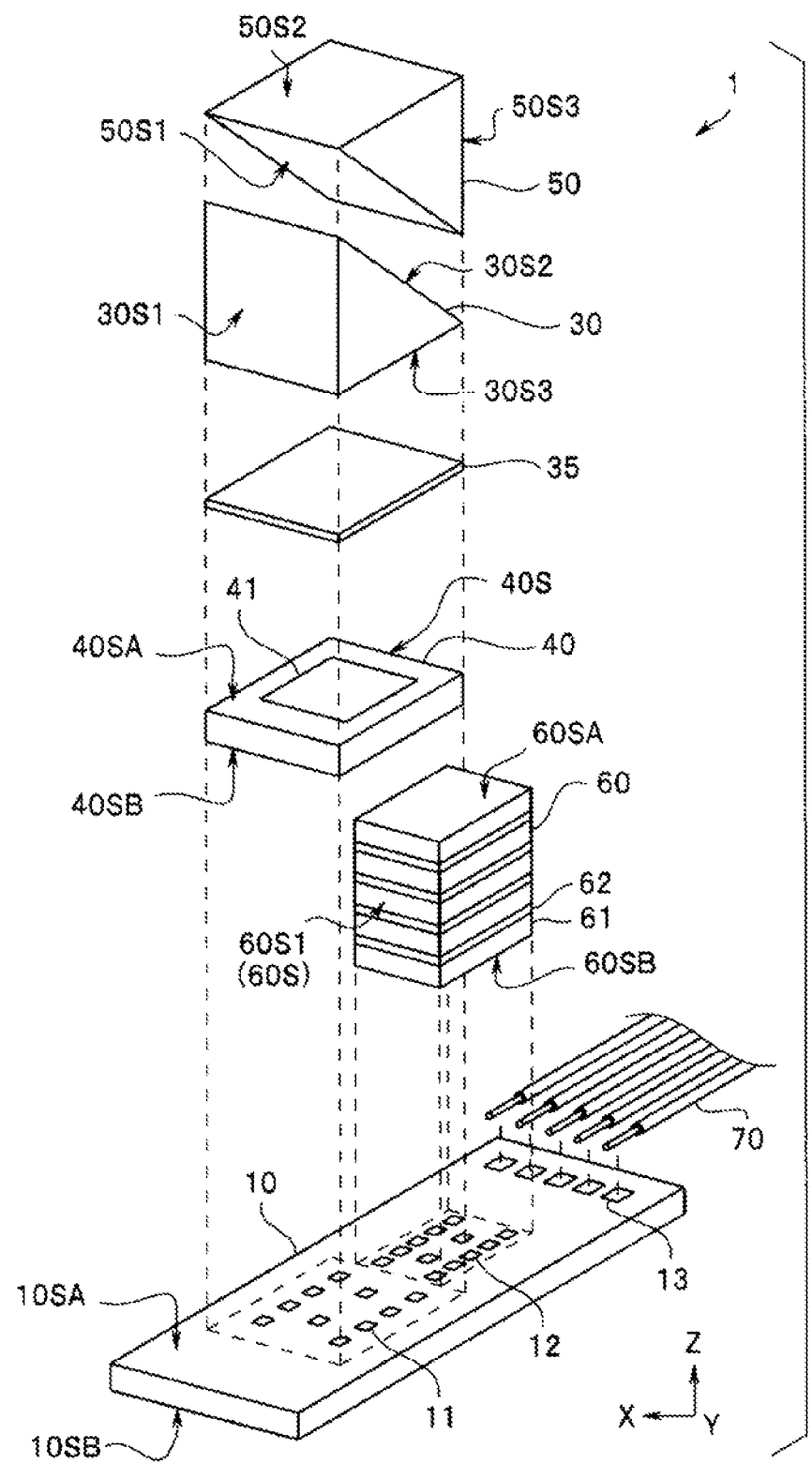
FIG. 4 is an exploded perspective view of the image capturing module according to the second embodiment.

As illustrated in FIGS. 2 through 4, an image capturing module 1 according to the present embodiment includes a wiring board 10, a prism 30, an image capturing element 40, a support member 50, and a layered element 60.

In the description that follows, figures based on various embodiments are schematic in nature. It should be noted that relations between thickness and width of various parts and thickness ratios and relative angles between various parts are different from those in reality. Different figures may contain portions representing different dimensional relations and ratios. In addition, some components may be omitted from illustration.

The wiring board 10 has a principal surface 10SA on which there are disposed a plurality of first electrodes 11 and a plurality of second electrodes 12. The wiring board 10 may be made of ceramics, glass, resin, fiber-reinforced resin, silicon, etc., and may be a multi-layer wiring board. Electronic parts such as chip capacitors, etc. may be mounted on the principal surface 10SA or an opposite surface 10SB that is opposite the principal surface 10SA.

The prism 30 is in the form of a rectangular prism having an entrance surface 30S1 to which light is applied, a reflection surface 30S2, and an exit surface 30S3 extending perpendicularly to the entrance surface 30S1.

The image capturing element 40 has a photodetection surface 40SA and a reverse surface 40SB that is opposite the photodetection surface 40SA. The photodetection surface 40SA includes a photodetector 41. A plurality of external electrodes 42 are disposed on the reverse surface 40SB. The image capturing element 40 that is made of a semiconductor such as silicon or the like is in the form of a charge-coupled device (CCD) or complementary metal oxide semiconductor (CMOS) image sensor with the photodetector 41 fabricated thereon according to a known semiconductor fabrication technology. The photodetector 41 and the external electrodes 42 are connected to each other by via interconnects, not illustrated.

The exit surface 30S3 of the prism 30 is bonded to the photodetection surface 40SA of the image capturing element 40 by an ultraviolet-curable transparent adhesive 35. The external electrodes 42 on the reverse surface 40SB are joined to the first electrodes 11 on the wiring board 10.

The prism 30 is ultra-small, and the exit surface 30S3 thereof is of an extremely small size of 500 μm square, for example. Therefore, the prism 30 is difficult to handle. For this reason, the support member 50 is bonded to the prism 30.

The support member 50 has an adhesion surface 50S1 parallel to the reflection surface 30S2 of the prism 30, an upper holding surface 50S2 parallel to the principal surface 10SA of the wiring board 10, and an abutment surface 50S3 perpendicular to the principal surface 10SA. The support member 50 is made of glass, ceramics, metal, or resin. The adhesion surface 50S1 of the support member 50 is bonded to the reflection surface 30S2 of the prism 30 by an adhesive layer, not illustrated.

For improved reflectance, a reflective film made of metal such as aluminum or the like may be disposed on the reflection surface 30S2, or the adhesive layer on the reflection surface 30S2 may be a black film.

Figure 6:
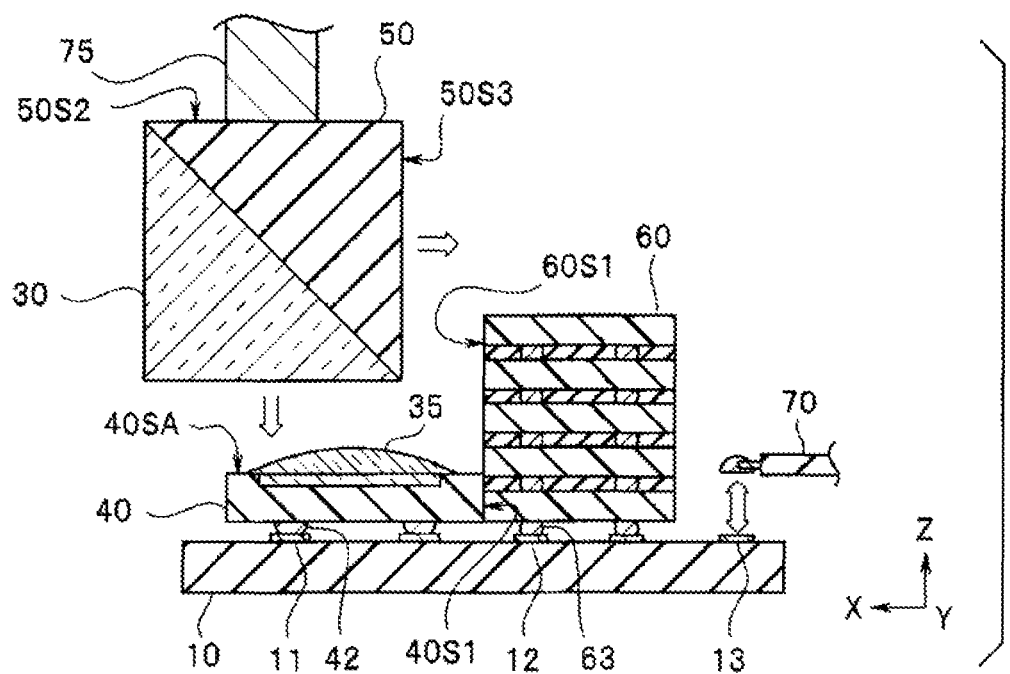
FIG. 6 is a cross-sectional view illustrating the method of manufacturing the image capturing module according to the second embodiment.

The prism 30 is stably held when the holding surface 50S2 of the support member 50 is attracted under suction by a handling jig 75 (see FIG. 6).

The layered element 60 includes a plurality of elements 61 layered together with sealing layers 62 interposed therebetween. The layered element 60 has an upper surface 60SA, a lower surface 60SB with element electrodes 63 disposed thereon, and a plurality of side surfaces 60S. The layered element 60 is shaped as a rectangular parallelepiped produced by cutting a layered wafer including a stack of semiconductor element wafers.

The semiconductor element elements 61 include a signal processing circuit, thin-film inductors, thin-film capacitors, an analog-to-digital converting circuit, etc. An image signal output from the image capturing element 40 is processed by the layered elements 60 that include those semiconductor elements 61 according to a primary signal processing process, and then transmitted through signal cables 70 joined to third electrodes 13 on the wiring board 10.

In the image capturing module 1, the abutment surface 50S3 of the support member 50 is held in abutment against a first side surface 60S1 among the side surfaces 60S of the layered element 60.

As described hereinafter, when the support member 50 that is bonded to the prism 30 is held in abutment against the first side surface 60S1 of the layered element 60 in advance mounted on the wiring board 10, positional matching in an optical axis O direction, i.e., an X-axis direction, is automatically achieved. Therefore, the image capturing module 1, though it is ultra-small, is easy to manufacture and has good optical characteristics as its optical path length is of a design value.

Method of Manufacturing the Image Capturing Module

Figure 5:
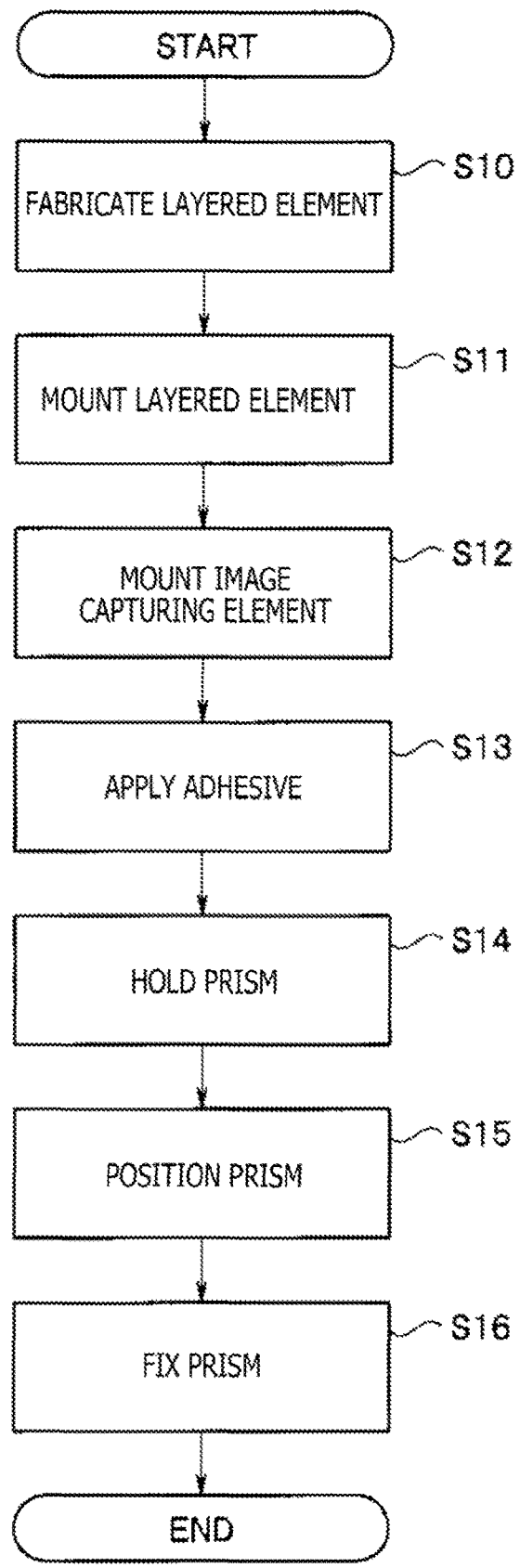
FIG. 5 is a flowchart illustrating a method of manufacturing the image capturing module according to the second embodiment.

Next, a method of manufacturing the image capturing module 1 will be described below with reference to a flowchart of FIG. 5.

Step S10: Fabrication of the Layered Element

As described hereinbefore, the layered element 60 is produced by cutting a layered wafer including a stack of semiconductor wafers. Therefore, the layered element 60 is shaped as a rectangular parallelepiped with the four side surfaces 60S being cut surfaces perpendicular to the upper surface 60SA and the lower surface 60SB.

The layered element 60 may be shaped as a substantially rectangular parallelepiped with side surface corners curved or as a hexagonal prism having six side surfaces with side surface corners beveled, insofar as the layered element 60 has the first side surface 60S1 against which at least a portion of the abutment surface S0S3 can be stably held in abutment.

Step S11: Mounting of the Layered Element

The layered element 60 is mounted on the principal surface 10SA of the wiring board 10. In the case of soldered joining, for example, the layered element 60 is positioned accurately in the position where the second electrodes 12 are disposed on the wiring board 10 due to a self-alignment effect.

Step S12: Mounting of the Image Capturing Element

The image capturing element 40 is mounted on the principal surface 10SA of the wiring board 10. The image capturing element 40 and the layered element 60 can be mounted relatively easily and accurately at predetermined positions on the principal surface 10SA of the wiring board 10.

In the image capturing module 1, the image capturing element 40 is disposed with a side surface thereof abutting against the first side surface 60S1 of the layered element 60. In other words, the position of the image capturing element 40 in the optical axis O direction is automatically determined by the first side surface 60S1 of the layered element 60.

Step S13: Application of an Adhesive

An uncured adhesive 35 is applied to the photodetection surface 40SA of the image capturing element 40. The adhesive 35 may be a transparent silicone resin, for example.

Step S14: Holding of the Prism with the Handling Jig 75

As illustrated in FIG. 6, the holding surface 50S2 of the support member 50 to which the prism 30 is bonded is attracted under suction and secured to the handling jig 75. Though the prism 30 is ultra-small, it can easily be handled by being secured to the handling jig 75.

The holding surface 50S2 may not necessarily be a flat surface, but may have a groove, a hole, or a wall insofar as it can stably be secured to the handling jig 75. Furthermore, the entrance surface 30S1 of the prism 30 and the abutment surface 50S3 of the support member 50 may be sandwiched by and secured to the handling jig 75.

Step S15: Positioning of the Prism

The uncured adhesive 35 has already been applied to the photodetection surface 40SA of the image capturing element 40. As illustrated in FIG. 6, the handling jig 75 is operated to place the prism 30 onto the photodetection surface 40SA such that the abutment surface 50S3 of the support member 50 abuts against the first side surface 60S1 of the layered element 60.

Step S16: Fixing of the Prism

The adhesive 35 is cured to fix the prism 30 to the photodetection surface 40SA. In the case where the adhesive 35 is an ultraviolet-curable resin, the adhesive 35 is irradiated with ultraviolet rays, so that the uncured liquid-phase adhesive 35 is turned into a solid adhesive layer. After the adhesive 35 has been cured, the handling jig 75 is removed.

In the case where the thickness of each element 61 is 50 μm and the thickness of each sealing layer 62 is 10 μm, for example, the height, i.e., a dimension in a Z-axis direction, of the layered element 60 that includes five elements 61 stacked is 290 μm. The upper surface 60SA has a size of 400 μm square. Therefore, the first side surface 60S1 of the layered element 60 has a size of 400×290 μm.

The holding surface 50S2 of the support member 50 has a size of 500×500 μm. When the abutment surface 50S3 of the support member 50 abuts against the first side surface 60S1 of the layered element 60, the support member 50 is automatically positioned in a predetermined position. Therefore, the image capturing module 1 is easy to manufacture.

The height, i.e., the dimension in the Z-axis direction, of the layered element 60 should preferably be equal to or larger than 25%, or more preferably 40%, of the height up to the holding surface 50S2 of the support member 50 for stable abutment of the support member 50 against the layered element 60. While the height of the layered element 60 is not limited to any particular value, it should preferably be equal to or smaller than 100% of the height of the support member 50 for making the image capturing module 1 smaller in diameter.

In order to keep the height of the layered element 60, a dummy element that has no particular function may be layered on the layered element 60.

Moreover, as described hereinbefore, in the image capturing module 1, the image capturing element 40 is positioned in the optical axis direction by the first side surface 60S1 of the layered element 60. In other words, the prism 30 and the image capturing element 40 have their positions defined in the optical axis direction accurately and easily with respect to the layered element 60.

Modifications of the Second Embodiment

Next, image capturing modules 1A through 1E according to modifications of the second embodiment will be described below. Since the image capturing modules 1A through 1E are similar to the image capturing module 1 and offer the same advantages as the image capturing module 1, those components which have the same functions are denoted by identical numeral reference, and will not be described below.

Modification 1 of the Second Embodiment

Figure 7:
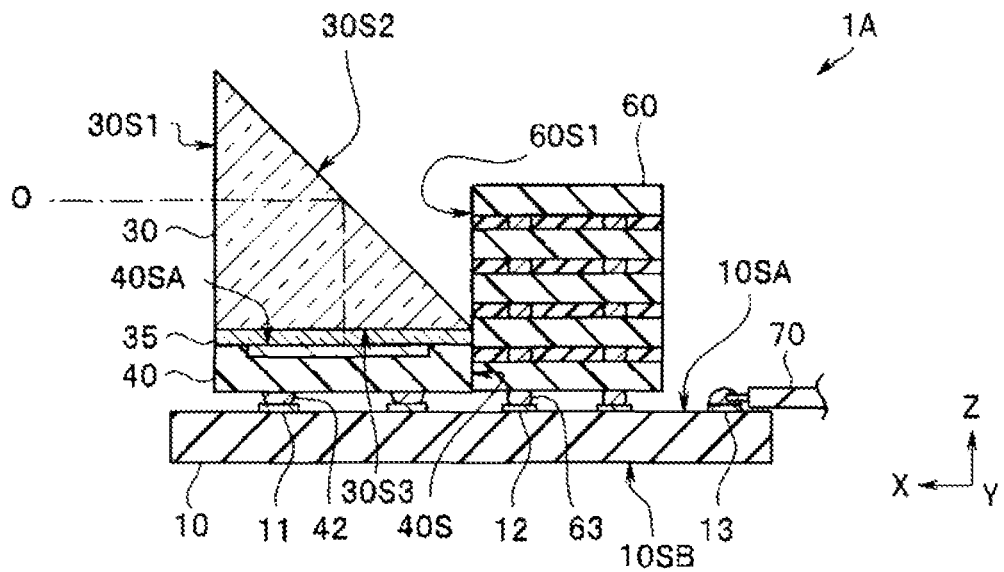
FIG. 7 is a cross-sectional view of an image capturing module according to modification 1 of the second embodiment.

As illustrated in FIG. 7, the image capturing module 1A according to the present modification is free of a support member for the prism 30. The prism 30 has a side where the reflection surface 30S2 and the exit surface 30S3 thereof intersect with each other, and the side abuts against the first side surface 60S1 of the layered element 60.

The prism may have an abutment surface parallel to the first side surface 60S1, and the abutment surface may abut against the first side surface 60S1.

Inasmuch as the position of the prism 30 in the optical axis O direction, i.e., the X-axis direction, is automatically defined by the layered element 60, the image capturing module 1A is easy to manufacture and has good optical characteristics.

Modification 2 of the Second Embodiment

Figure 8:
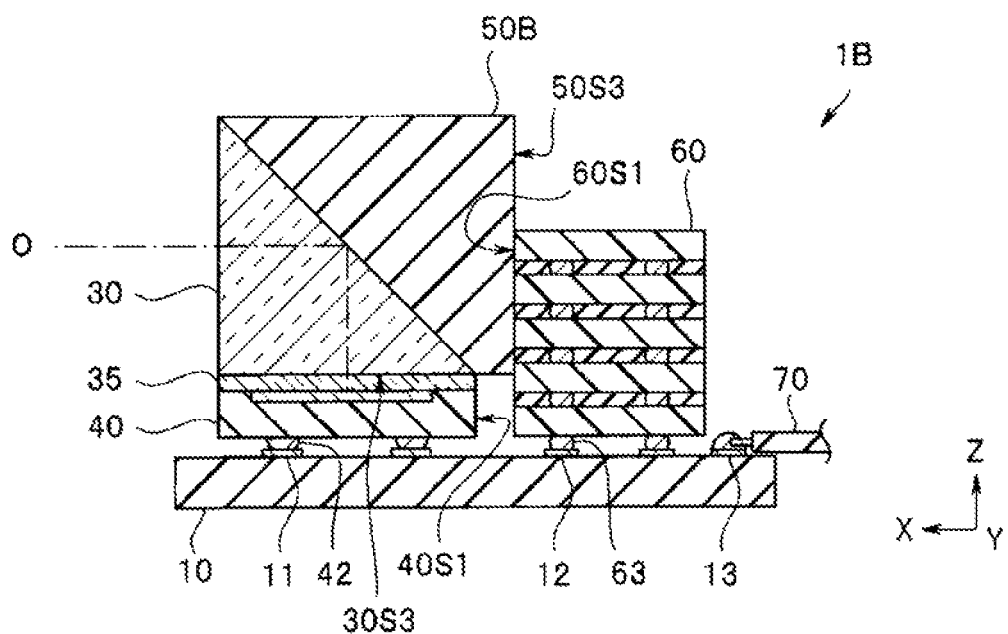
FIG. 8 is a cross-sectional view of an image capturing module according to modification 2 of the second embodiment.

As illustrated in FIG. 8, the image capturing module 1B according to the present modification includes a support member 50B having an abutment surface 50S3 that projects from the exit surface 30S3 of the prism 30 toward the layered element 60. Therefore, the side surface 40S1 of the image capturing element 40 may be kept out of abutment against the first side surface 60S1 of the layered element 60. In other words, a gap is defined between the side surface 40S1 of the image capturing element 40 and the first side surface 60S1 of the layered element 60.

As the area of the holding surface 50S2 of the image capturing module 1B is larger than the corresponding area of the image capturing module 1, it is easier to secure the handling jig 75 than with the image capturing module 1.

Modification 3 of the Second Embodiment

Figure 9:
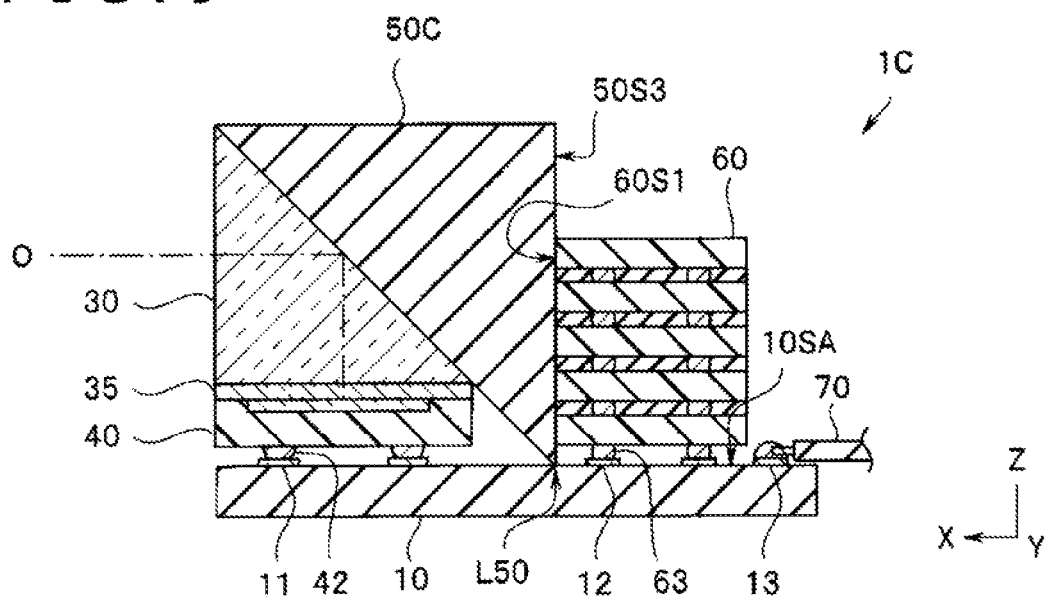
FIG. 9 is a cross-sectional view of an image capturing module according to modification 3 of the second embodiment.

As illustrated in FIG. 9, the image capturing module 1C according to the present modification includes a support member 50C having an abutment surface 50S3 that projects from the exit surface 30S3 of the prism 30 toward the layered element 60. In addition, the support member 50C has a bottom side L50 held in abutment against the principal surface 10SA of the wiring board 10. The support member 50B may have a bottom surface parallel to the principal surface 10SA of the wiring board 10 and held in abutment against the principal surface 10SA.

Not only the position of the prism 30 in the optical axis O direction, i.e., the X-axis direction, but also the position thereof in the heightwise direction, i.e., the Z-axis direction, or the thickness of the adhesive layer 35, are defined by the support member 50.

Modification 4 of the Second Embodiment

Figure 10:
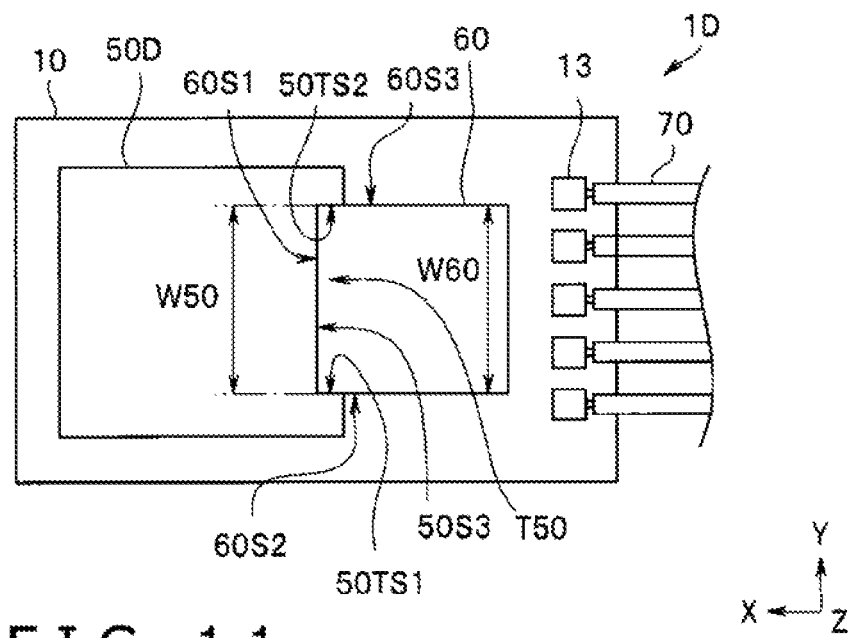
FIG. 10 is a plan view of an image capturing module according to modification 4 of the second embodiment.
Figure 11:
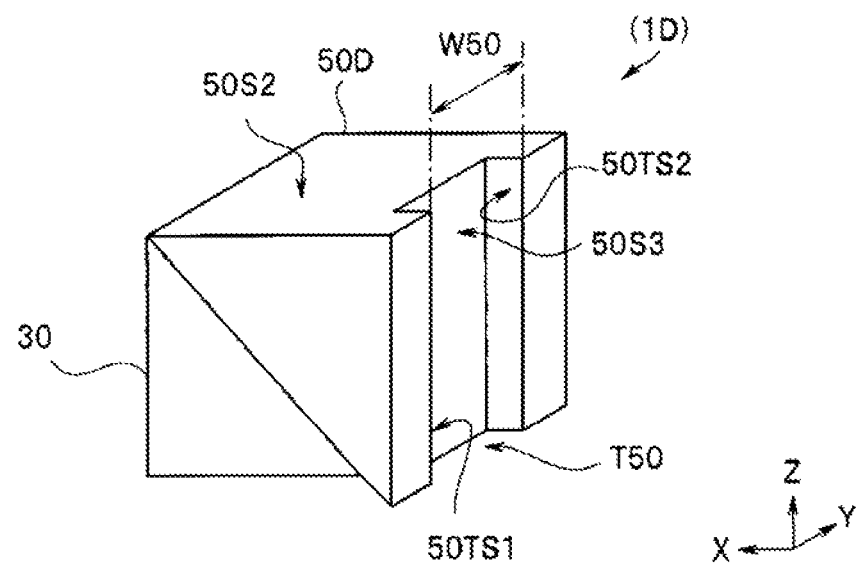
FIG. 11 is a perspective view of a prism to which there is bonded a support member of the image capturing module according to modification 4 of the second embodiment.

As illustrated in FIGS. 10 and 11, the image capturing module 1D according to the present modification includes a support member 50D having a recess T50 defined in the abutment surface 50S3. The recess T50 has a wall surface 50TS1 held in abutment against the second side surface 60S2 of the layered element 60 that is perpendicular to the first side surface 60S1 thereof. The recess T50 also has a wall surface 50TS2 held in abutment against the third side surface 60S3 of the layered element 60 that is opposite the second side surface 60S2 thereof.

The recess T50 is in the form of a groove extending in the heightwise direction, i.e., the Z-axis direction, and has a width W50 identical to a width W60 of the layered element 60. In other words, the layered element 60 is fitted in the recess T50 in the support member 50C.

The position of the prism 30 in a lateral direction, i.e., a Y-axis direction, is also defined by the layered element 60.

For defining the position in the lateral direction, the prism 30 may be held in abutment against either one of the second side surface 60S2 and the third side surface 60S3 that lie perpendicularly to the first side surface 60S1 of the layered element 60. In other words, the width W50 of the recess T50 may be larger than the width W60 of the layered element 60.

Furthermore, as is the case with the image capturing module 1C according to modification 3, the position of the prism 30 in the heightwise direction, i.e., the Z-axis direction, may be defined by the support member 50.

Modification 5 of the Second Embodiment

Figure 12:
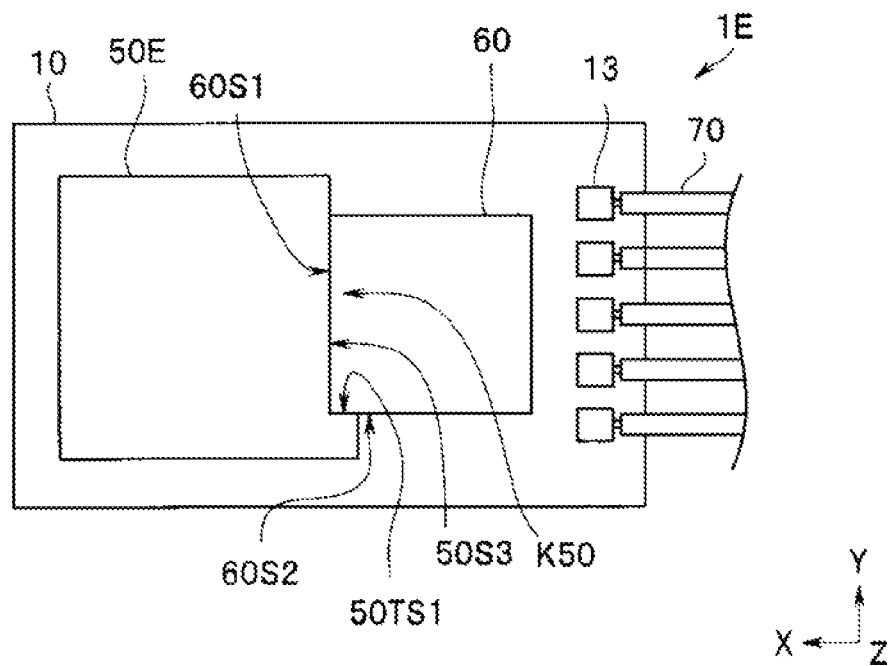
FIG. 12 is a plan view of an image capturing module according to modification 5 of the second embodiment.
Figure 13:
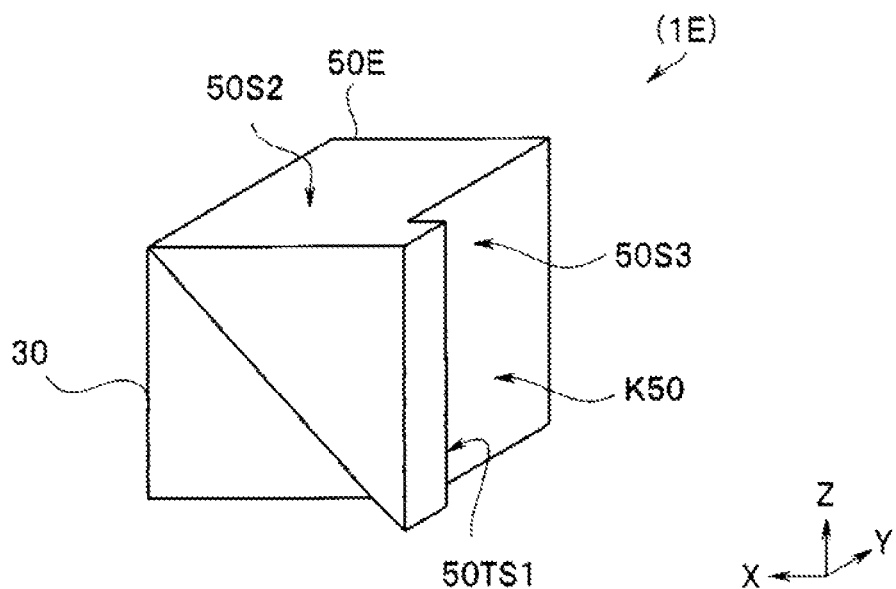
FIG. 13 is a perspective view of a prism to which there is bonded a support member of the image capturing module according to modification 5 of the second embodiment.

As illustrated in FIGS. 12 and 13, the image capturing module 1E according to the present modification includes a support member 50E having a cut-out portion K50 defined in the abutment surface 50S3, in place of the recess T50 defined in the support member 50D of the image capturing module 1D. The cut-out portion K50 is of an L shape as viewed in plan. The cut-out portion K50 has a wall surface 50TS1 is held in abutment against the second side surface 60S2 of the layered element 60 that is perpendicular to the first side surface 60S1 thereof. In the image capturing module 1E, as with the image capturing module 1D, the position of the prism 30 or the support member 50E in the lateral direction, i.e., the Y-axis direction, is also defined by the layered element 60.

It is needless to say that endoscopes that incorporate the image capturing modules 1A through 1E according to the modifications offer the advantages of image capturing modules according to the modifications.

The disclosed technology is not limited to the embodiments described hereinbefore, but various changes, combinations, and applications of the embodiments may be made without departing from the scope of the invention.

In sum, one aspect of the disclosed technology is directed to an endoscope system comprising an endoscope having an insertion portion. The insertion portion includes opposed respective distal and proximal ends. The endoscope is attached to the proximal end of the insertion portion and an image capturing module is attached to the distal-end portion of an insertion portion. The image capturing module includes a wiring board having a principal surface including first electrodes and second electrodes disposed thereon. An image capturing element having opposed surfaces defined by respective photodetection and reverse surfaces. The reverse surface includes external electrodes that is disposed thereon and is connected to the first electrodes on the wiring board. A prism having an entrance surface to which light is applied, a reflection surface, and an exit surface in which the exit surface being bonded to the photodetection surface of the image capturing element. A support member is used to support the prism. A layered element including a plurality of elements is layered together and having an upper surface, a lower surface with element electrodes disposed thereon, and a plurality of side surfaces. The element electrodes is joined to the second electrodes on the wiring board. At least a portion of the support member is held in abutment against a first side surface among the plurality of side surfaces of the layered element.

The support member has an adhesion surface parallel to the reflection surface of the prism, an upper holding surface parallel to the principal surface, and an abutment surface perpendicular to the principal surface. The adhesion surface is bonded to the reflection surface of the prism. At least a portion of the abutment surface of the support member is held in abutment against the first side surface among the plurality of side surfaces of the layered element. A gap is defined between a side surface of the image capturing element and the first side surface of the layered element. The abutment surface of the support member has a recess defined therein. The recess having a wall surface held in abutment against a second side surface of the layered element that is perpendicular to the first side surface thereof. The abutment surface of the support member has a cut-out portion defined therein. The cut-out portion is of an L- shaped as viewed in plan. The cut-out portion has a wall surface held in abutment against a second side surface of the layered element that is perpendicular to the first side surface thereof. The support member has a bottom side held in abutment against the principal surface of the wiring board. The endoscope system further comprises an operating portion and a universal cord being attached to the operating portion.

Another aspect of the disclosed technology is directed to an endoscope system having an image capturing module. The image capturing module comprises a wiring board having a principal surface including first electrodes and second electrodes disposed thereon. An image capturing element having opposed surfaces defined by respective photodetection and reverse surfaces. The reverse surface includes external electrodes that is connected to the first electrodes on the wiring board. A prism having an entrance surface to which light is applied, a reflection surface, and an exit surface in which the exit surface is bonded to the photodetection surface of the image capturing element. A support member having an adhesion surface parallel to the reflection surface of the prism, an upper holding surface parallel to the principal surface, and an abutment surface perpendicular to the principal surface. The adhesion surface is bonded to the reflection surface of the prism. A layered element including a plurality of elements layered together and having an upper surface, a lower surface with element electrodes disposed thereon, and a plurality of side surfaces. The element electrodes is joined to the second electrodes on the wiring board. At least a portion of the abutment surface of the support member is held in abutment against a first side surface among the plurality of side surfaces of the layered element.

A further aspect of the disclosed technology is directed to an endoscope system having an image capturing module. The image capturing module comprises a wiring board having a principal surface including first electrodes and second electrodes disposed thereon. An image capturing element having opposed surfaces defined by respective photodetection and reverse surfaces. The reverse surface includes external electrodes being connected to the first electrodes on the wiring board. A prism having an entrance surface to which light is applied, a reflection surface, and an exit surface in which the exit surface being bonded to the photodetection surface of the image capturing element. A layered element including a plurality of elements layered together and having an upper surface, a lower surface with element electrodes disposed thereon, and a plurality of side surfaces. The element electrodes being joined to the second electrodes on the wiring board. The prism has a side where the reflection surface and the exit surface thereof intersect with one another. The side is abutting against a first side surface among the plurality of side surfaces of the layered element.

A further aspect of the disclosed technology is directed to an endoscope system having an image capturing module. The image capturing module comprises a wiring board having a principal surface including first electrodes and second electrodes disposed thereon. An image capturing element having opposed surfaces defined by respective photodetection and reverse surfaces. The reverse surface includes external electrodes being connected to the first electrodes on the wiring board. The prism having an entrance surface to which light is applied, a reflection surface, and an exit surface in which the exit surface is bonded to the photodetection surface of the image capturing element. A layered element including a plurality of elements layered together and having an upper surface, a lower surface with element electrodes disposed thereon, and a plurality of side surfaces. The element electrodes being joined to the second electrodes on the wiring board. The prism has an abutment surface parallel to a first side surface among the plurality of side surfaces of the layered element and held in abutment against the first side surface.

Yet, a further aspect of the disclosed technology is directed to a method of manufacturing an endoscope having an image capturing module. The method comprises mounting a layered element including a plurality of elements layered together on a wiring board with electrodes disposed thereon; mounting an image capturing element on the wiring board; applying an uncured adhesive to a photodetection surface of the image capturing element; moving a support member that supports a prism such that at least a portion of the support member abuts against a first side surface of the layered element, and placing the prism on the photodetection surface; and curing the adhesive.

While various embodiments of the disclosed technology have been described above, it should be understood that they have been presented by way of example only, and not of limitation. Likewise, the various diagrams may depict an example schematic or other configuration for the disclosed technology, which is done to aid in understanding the features and functionality that can be included in the disclosed technology. The disclosed technology is not restricted to the illustrated example schematic or configurations, but the desired features can be implemented using a variety of alternative illustrations and configurations. Indeed, it will be apparent to one of skill in the art how alternative functional, logical or physical locations and configurations can be implemented to implement the desired features of the technology disclosed herein.

Although the disclosed technology is described above in terms of various exemplary embodiments and implementations, it should be understood that the various features, aspects and functionality described in one or more of the individual embodiments are not limited in their applicability to the particular embodiment with which they are described, but instead can be applied, alone or in various combinations, to one or more of the other embodiments of the disclosed technology, whether or not such embodiments are described and whether or not such features are presented as being a part of a described embodiment. Thus, the breadth and scope of the technology disclosed herein should not be limited by any of the above-described exemplary embodiments.

Terms and phrases used in this document, and variations thereof, unless otherwise expressly stated, should be construed as open ended as opposed to limiting. As examples of the foregoing: the term "including" should be read as meaning "including, without limitation" or the like; the term "example" is used to provide exemplary instances of the item in discussion, not an exhaustive or limiting list thereof; the terms "a" or "an" should be read as meaning "at least one," "one or more" or the like; and adjectives such as "conventional," "traditional," "normal," "standard," "known" and terms of similar meaning should not be construed as limiting the item described to a given time period or to an item available as of a given time, but instead should be read to encompass conventional, traditional, normal, or standard technologies that may be available or known now or at any time in the future. Likewise, where this document refers to technologies that would be apparent or known to one of ordinary skill in the art, such technologies encompass those apparent or known to the skilled artisan now or at any time in the future.

The presence of broadening words and phrases such as "one or more," "at least," "but not limited to" or other like phrases in some instances shall not be read to mean that the narrower case is intended or required in instances where such broadening phrases may be absent.

Additionally, the various embodiments set forth herein are described in terms of exemplary schematics, block diagrams, and other illustrations. As will become apparent to one of ordinary skill in the art after reading this document, the illustrated embodiments and their various alternatives can be implemented without confinement to the illustrated examples. For example, block diagrams and their accompanying description should not be construed as mandating a particular configuration.

What is claimed is:

1. An endoscope comprising:
   an insertion portion having a distal end portion and a proximal end portion; and
   an image capturing module being disposed at the distal-end portion of the insertion portion, wherein the image capturing module comprises:
   a wiring board having a principal surface including first electrodes and second electrodes disposed on the principal surface,
   an image sensor having a photodetection surface and a reverse surface opposing the photodetection surface, the reverse surface including external electrodes connected to the first electrodes on the wiring board,
   a prism having an entrance surface to which light is applied, a reflection surface, and an exit surface wherein the exit surface being bonded to the photodetection surface of the image sensor,
   a support configured to support the prism, and
   a layered element including a plurality of semiconductor elements layered together, the layered element having an upper surface, a lower surface with element electrodes disposed on the lower surface, and a plurality of side surfaces, the element electrodes being joined to the second electrodes on the wiring board,
   wherein the support has an adhesion surface parallel to the reflection surface of the prism, an upper holding surface parallel to the principal surface, and an abutment surface perpendicular to the principal surface, the adhesion surface being bonded to the reflection surface of the prism to fix the support to the prism such that at least a portion of the abutment surface of the support abuts against a first side surface among the plurality of side surfaces of the layered element.

2. The endoscope of claim 1, wherein the support is configured such that a gap is defined between a side surface of the image capturing element and the first side surface of the layered element.

3. The endoscope of claim 1 further comprising:
   an operating portion disposed at the proximal end portion of the insertion section; and
   a universal cord being attached to the operating portion.

4. An insertion section for use with an endoscope, the insertion section comprising:
   an image capturing module, the image capturing module comprising:

a wiring board having a principal surface including first electrodes and second electrodes disposed on the principal surface;

an image sensor having a photodetection surface and a reverse surface opposing the photodetection surface, the reverse surface including external electrodes connected to the first electrodes on the wiring board;

a prism having an entrance surface to which light is applied, a reflection surface, and an exit surface wherein the exit surface being bonded to the photodetection surface of the image sensor;

a support having an adhesion surface parallel to the reflection surface of the prism, an upper holding surface parallel to the principal surface, and an abutment surface perpendicular to the principal surface, the adhesion surface being bonded to the reflection surface of the prism; and a layered element including a plurality of semiconductor elements layered together, the layered element having an upper surface, a lower surface with element electrodes disposed on the lower surface, and a plurality of side surfaces, the element electrodes being joined to the second electrodes on the wiring board, wherein the adhesion surface is bonded to the reflection surface of the prism to fix the support to the prism such that at least a portion of the abutment surface of the support abuts against a first side surface among the plurality of side surfaces of the layered element.

5. A method of manufacturing an image capturing module, the method comprising:

mounting a layered element including a plurality of semiconductor elements layered together on a wiring board with electrodes disposed thereon;

mounting an image sensor on the wiring board;

applying an uncured adhesive to a photodetection surface of the image sensor;

holding a support that supports a prism by attaching a handling jig to an upper holding surface of the support;

moving the support while being held by the jig such that at least a portion of an abutment surface of the support abuts against a first side surface of the layered element;

placing the prism on the adhesive applied to the photodetection surface while the abutment surface of the support abuts against the first side surface of the layered element; and curing the adhesive;

wherein the wiring board has a principal surface including first electrodes and second electrodes disposed on the principal surface, the image sensor includes the photodetection surface and a reverse surface opposing the photodetection surface, the reverse surface including external electrodes being connected to the first electrodes on the wiring board, the prism includes an entrance surface to which light is applied, a reflection surface, and an exit surface wherein the exit surface being bonded to the photodetection surface of the image sensor, and the support member includes an adhesion surface parallel to the reflection surface of the prism, the upper holding surface parallel to the principal surface, and the abutment surface perpendicular to the principal surface wherein the adhesion surface being bonded to the reflection surface of the prism.

6. The insertion section of claim 4, wherein the support is configured such that a gap is defined between a side surface of the image capturing element and the first side surface of the layered element.

7. The method of claim 5, wherein the placing comprises placing the prism on the adhesive applied to the photodetection surface while the abutment surface of the support abuts against the first side surface of the layered element such that a gap is defined between a side surface of the image capturing element and the first side surface of the layered element.

8. An image capturing module comprising:

a wiring board having a principal surface including first electrodes and second electrodes disposed on the principal surface, an image sensor having a photodetection surface and a reverse surface opposing the photodetection surface, the reverse surface including external electrodes connected to the first electrodes on the wiring board, a prism having an entrance surface to which light is applied, a reflection surface, and an exit surface, wherein the exit surface being bonded to the photodetection surface of the image sensor, a support configured to support the prism, and a layered element including a plurality of semiconductor elements layered together, the layered element having an upper surface, a lower surface with element electrodes disposed on the lower surface, and a plurality of side surfaces, the element electrodes being joined to the second electrodes on the wiring board, wherein the support has an adhesion surface parallel to the reflection surface of the prism, an upper holding surface parallel to the principal surface, and an abutment surface perpendicular to the principal surface, the adhesion surface being bonded to the reflection surface of the prism to fix the support to the prism such that at least a portion of the abutment surface of the support abuts against a first side surface among the plurality of side surfaces of the layered element.

9. The image capturing module of claim 8, wherein the support is configured such that a gap is defined between a side surface of the image capturing element and the first side surface of the layered element.

* * * * *